US011633452B2

(12) United States Patent
Hodgdon et al.

(10) Patent No.: US 11,633,452 B2
(45) Date of Patent: *Apr. 25, 2023

(54) COMPOSITIONS AND METHODS FOR TREATING VAGINAL DRYNESS

(71) Applicant: The Procter & Gamble Company, Cincinnati, OH (US)

(72) Inventors: Travis Kyle Hodgdon, Cincinnati, OH (US); Leo Timothy Laughlin, II, Mason, OH (US); Samantha Chen-Yee Wang, Cincinnati, OH (US); Robert Lloyd Binder, Montgomery, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 80 days.

This patent is subject to a terminal disclaimer.

(21) Appl. No.: 17/080,930

(22) Filed: Oct. 27, 2020

(65) Prior Publication Data
US 2021/0038679 A1 Feb. 11, 2021

Related U.S. Application Data

(63) Continuation of application No. PCT/US2019/030532, filed on May 3, 2019.

(60) Provisional application No. 62/676,068, filed on May 24, 2018, provisional application No. 62/666,958, filed on May 4, 2018.

(51) Int. Cl.
A61K 38/08 (2019.01)
A61P 15/02 (2006.01)
A61K 9/107 (2006.01)
A61K 31/198 (2006.01)
A61K 31/355 (2006.01)
A61K 38/06 (2006.01)
A61K 47/44 (2017.01)
A61K 9/16 (2006.01)
A61K 31/047 (2006.01)
A61K 31/407 (2006.01)
A61K 36/22 (2006.01)
A61K 36/48 (2006.01)
A61K 36/49 (2006.01)
A61K 36/54 (2006.01)
A61K 36/899 (2006.01)

(52) U.S. Cl.
CPC .............. A61K 38/08 (2013.01); A61K 9/107 (2013.01); A61K 9/1641 (2013.01); A61K 31/047 (2013.01); A61K 31/198 (2013.01); A61K 31/355 (2013.01); A61K 31/407 (2013.01); A61K 36/22 (2013.01); A61K 36/48 (2013.01); A61K 36/49 (2013.01); A61K 36/54 (2013.01); A61K 36/899 (2013.01); A61K 38/06 (2013.01); A61K 47/44 (2013.01); A61P 15/02 (2018.01)

(58) Field of Classification Search
None
See application file for complete search history.

(56) References Cited

U.S. PATENT DOCUMENTS

| | | | | |
|---|---|---|---|---|
| 5,015,474 A | * | 5/1991 | Parnell | A61K 9/02 424/DIG. 15 |
| 7,275,486 B2 | * | 10/2007 | Hsieh | F42B 8/26 102/482 |
| 7,767,215 B2 | * | 8/2010 | McClellan | A61P 17/02 514/474 |
| 2005/0089537 A1 | * | 4/2005 | Birnholz | A61K 9/0034 424/401 |
| 2009/0035361 A1 | | 2/2009 | Schiena | |
| 2010/0105784 A1 | * | 4/2010 | Remon | A61K 9/0034 514/778 |
| 2012/0083747 A1 | | 4/2012 | Galland | |
| 2014/0309173 A1 | * | 10/2014 | Dreher | A61K 31/4172 548/339.1 |
| 2014/0322329 A1 | | 10/2014 | Bartorelli | |
| 2014/0343134 A1 | | 11/2014 | Ferrari | |
| 2015/0202211 A1 | | 7/2015 | Amadio | |
| 2019/0224213 A1 | | 7/2019 | Colli | |
| 2021/0038632 A1 | | 2/2021 | Hodgdon et al. | |

FOREIGN PATENT DOCUMENTS

| | | |
|---|---|---|
| CN | 1509753 A | 7/2004 |
| CN | 1678261 A | 10/2005 |
| CN | 102170862 A | 8/2011 |
| CN | 103341092 A | 10/2013 |
| KR | 20160119347 A | 10/2016 |

(Continued)

OTHER PUBLICATIONS

An (The effect of glycerin, hyaluronic acid and silicone oil on the hydration, moisturization and trans epidermal water loss in human skin, Asian Journal of Beauty and Cosmetology, Published 2013). (Year: 2013).*

(Continued)

Primary Examiner — Melissa S Mercier
(74) Attorney, Agent, or Firm — Melissa G. Krasovec

(57) ABSTRACT

A method of treating vaginal dryness by administering a vaginal care composition, which includes an effective amount of a vaginal care agent, to vaginal tissue of a user experiencing vaginal dryness. The vaginal care agent may be selected to specifically treat symptoms of vaginal dryness exhibited by the introitus and/or labia, based on the transcriptomic data of skin cells obtained therefrom. In some instances, the vaginal care composition may be applied to introitus and/or labia with a suitable implement configured for such use.

17 Claims, No Drawings

(56) References Cited

FOREIGN PATENT DOCUMENTS

| PL | 416198 A1 | 8/2017 | | |
|---|---|---|---|---|
| WO | 2007039124 A2 | 4/2007 | | |
| WO | WO-2007039124 A2 | * | 4/2007 | ........... A61K 31/728 |

OTHER PUBLICATIONS

Anti-inflammatory and anti-bacterial properties of tetramethyihexadecenyl Dec. 31, 2015succinyl cysteine (TSC): a skin-protecting cosmetic functional ingredient, J.R. Fernandez et al., International Journal of cosmetic Science 37, year 2015 pp. 129-133.
Ghazanfarpour et al., "Effects of Flaxseed and Hypericum Perforatum on Hot Flash, Vaginalatrophy and Estrogen-Dependent Cancers in Menopausal Women: A Systematic Review and Meta-Analysis", Avicenna Journal of Phytomedicine, Vo. 6, No. 3, May-Jun. 2016, pp. 273-283.
International Search Report and Written Opinion; Appl. No. PCT/US2019/030518; dated Jul. 12, 2019; 14 pages.
International Search Report and Written Opinion; Appl. No. PCT/US2019/030532; dated Jul. 24, 2019; 15 pages.
U.S. Appl. No. 17/080,925, filed Oct. 27, 2020, Travis Kyle Hodgdon, et al.
AN 2016-649811; Database WPI Week 201683, Thomson Scientific, London, GB; XP002792601, Publication date Oct. 13, 2016.
AN 2018-233398; Database WPI Week 201826; Thomson Scientific, London, GB; XP002792799, Publication date Aug. 28, 2017.

* cited by examiner

COMPOSITIONS AND METHODS FOR TREATING VAGINAL DRYNESS

TECHNICAL FIELD

Compositions and methods for treating vaginal dryness are generally provided.

BACKGROUND

Estimates indicate that by 2030 there will be about 1.2 billion menopausal and post-menopausal women in the world. Given that the average age at which menopause occurs has remained the same and life expectancy among women has generally increased, the number of post-menopausal women is expected to grow. As such, there is increasing concern surrounding the conditions and symptoms experienced by peri-menopausal, menopausal, post-menopausal women, and thus the need for treatment is growing as well.

It is well known that menopause is associated with a decrease in estrogen production, which can result in vaginal atrophy and vaginal dryness. Vaginal dryness can also result from a variety of other physical and/or mental conditions such as medications, decreased estrogen levels due to non-menopausal factors (e.g., childbirth, breastfeeding, smoking, surgery), personal hygiene products and practices, anxiety, stress, and decreased libido. Symptoms of vaginal dryness can include soreness, itching, burning, painful intercourse, and mild discharge. A variety of solutions have been proposed to address vaginal dryness associated with vaginal atrophy, such as, for example, applying prescription-based remedies (e.g., an estrogen supplement with or without progesterone, sometimes referred to as hormone replacement therapy or HRT) deep within the vaginal canal using a plunger or medicated ring type applicator. While such treatments have shown positive effects in the treatment of vaginal dryness, some women continue to experience symptoms. Additionally, the medications used in these types of treatments may be prohibitively expensive.

Further, HRT has also been reduced by contraindications such as a history of cancer and thromboembolism. Thus, non-hormonal treatment methods may be preferred by some women.

Several over-the-counter solutions have been offered to consumers to treat various symptoms and/or conditions of vaginal dryness. These include vaginal moisturizers (e.g., Replens® Long Lasting Moisturizer and Replens® Moisture Restore External Comfort Gel, or HyaloGyn/HyaloFemme, available from Fidia Farmaceutici SpA and both supplied with disposable applicators to place in the vaginal canal), lubricants for reducing discomfort during intimacy (e.g., Replens® Silky Smooth Personal Lubricant, Astroglide®, K-Y® gels and lubricants), wipes (e.g., Vagisil® Anti-Itch Medicated Wipes), sprays, and washes and douches for eliminating bacteria that can cause unpleasant odors (e.g., Summer's Eve®). The Replens® Long Lasting Moisturizer, available from Church & Dwight, Inc., is provided with a plunger type applicator for depositing the moisturizer within the vaginal canal. The makers of Replens® have published several studies regarding the benefits of using the Replens® Long Lasting Moisturizer (see, e.g., womenshealthcaresolutions.com).

However, there remains a need for improved methods of treating vaginal dryness. Accordingly, it would be desirable to identify new vaginal care agents that treat or ameliorate one or more symptoms associated with vaginal dryness. It would also be desirable to provide a method of treating vaginal dryness that does not involve applying a vaginal care composition to a proximal portion of the vagina with an applicator. It would further be desirable to provide a method of treating vaginal dryness that involves applying a vaginal care composition to the labia and/or introitus.

SUMMARY

Disclosed herein is a method of treating vaginal dryness. The method comprises administering a vaginal care composition to vaginal tissue of a user experiencing vaginal dryness. The composition includes an effective amount of at least one vaginal care agent, which may be selected to specifically treat the introitus and/or labia. The vaginal care agent may be selected from di sodium tetramethylhexadecenyl succinyl cysteine, *Castanea sativa*, *Myrocarpus frondosus*, *Myrocarpus fastigiatus*, *Pistacia lentiscus* gum oil, glyceryl monoricinoleate, pentapeptide-28, *Cinnamomum cassia*, bamboo, *Paeonia suffruticosa*, hydroxydecyl ubiquinone, myristoyl octapeptide-1, hydrolyzed soybean fiber, yeast extract, hexapeptide-9, geranyllinalool, *Gelidium cartilagineum*, menthyl anthranilate, *Oenothera biennis*, hyaluronic acid, tetrapeptide-21, proanthocyanidin A, arginine aminobenzoate, a mixture of glycolic acid, ascorbyl tetraisopalmitate, and kojic acid, *Brassica rapa*, farnesene, dehydrocholesterol, javanol, *Ballota pseudodictamus*, dipropyl-7-methylxanthine, *Stachys byzantina*, 2-decanone, a mixture of biotin, linoleic acid, vitamin E, panthenol, and caffeine, a mixture of propanediol, lysine, lecithin, phenoxyethanol, tripeptide-9, and citrulline, acetyl tetrapeptide-11, algae extracts, piroctone olamine, and derivatives and combinations of these.

DETAILED DESCRIPTION

Chronic vaginal dryness can reduce the quality of life of women, especially menopausal or post-menopausal women who are more likely to experience chronic vaginal dryness than pre-menopausal women. Clinical manifestations of chronic vaginal dryness appear more dominant in the distal portion of the vagina (i.e., introitus) than the proximal portion (i.e., closer to the cervix), which is where some conventional treatments are applied. Treating the symptoms of vaginal dryness commonly involves placing a mucosal-adhesive vaginal care agent within the vaginal canal, for example, with a plunger-type applicator. Not surprisingly, such conventional methods of treatment have a variety of consumer drawbacks.

It has been discovered that symptoms of vaginal dryness may be treatable without the need to apply an active within the vaginal canal, thereby avoiding some of the undesirable drawbacks of conventional treatments. Transcriptomic data analysis suggests that changes occurring at the genetic level in distal vaginal tissue (i.e., introitus) and proximal vaginal tissue (i.e., more than 35 mm into the vaginal canal) are substantially the same for post-menopausal women. Surprisingly, transcriptomic data analysis also suggest that genetic changes exhibited at the introitus in post-menopausal women are markedly different from the genetic changes exhibited by the labia. In view of this unexpected finding, an improved method of treating vaginal dryness may be provided by treating the labia and/or introitus with a vaginal care composition specifically tailored to treat the unique changes in gene expression occurring in each area.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

All percentages disclosed herein are by weight of the vaginal care composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The vaginal care compositions herein can comprise, consist essentially of, or consist of, the components as well as optional ingredients described herein. As used herein, "consisting essentially of" means that the composition, method, or components thereof may include additional ingredients or features, but only if the additional ingredients or features do not materially alter the basic and novel characteristics of the claimed compositions or methods. As used in the description and the appended claims, the singular forms "a," "an," and "the" are intended to include the plural forms as well, unless the context clearly indicates otherwise.

"About" when used in the context of a parameter or range means a value that is within 30% of the stated value (e.g., with 25%, 20%, 15%, 10%, 5%, 2% or even within 1%).

"Benchmark agent" means any chemical, compound, environmental factor, small or large molecule, extract, formulation, or combinations thereof that is (are) known to induce or cause a superior effect (positive or negative) on the gene expression of a vaginal dryness condition.

"Control sample" means a matched sample (e.g., the same cell type used to generate the gene expression measurements for the plurality of biological conditions) that is identified as not including vaginal dryness. For example, the gene expression measurements from a control sample may be generated from a biological sample taken earlier in time, prior to exhibiting vaginal dryness; a control subject or population whose gene expression measurements are known; or an index value or baseline value. A control gene expression profile can also be derived from prediction algorithms or computed indices from population studies. In various embodiments, the control sample is matched for race, gender, age, geographic location, and/or ethnic origin with respect to origin of the gene expression measurements of the plurality of biological disorders.

"Derivative" means a molecule similar to that of another one, but differing from it with respect to a certain functional moiety (e.g., esters, ethers, amides, amines, carboxylic acids, hydroxyls, acetyls, thiols, halogens, and/or salts of the relevant molecule).

"Dermatologically acceptable" means that the compositions or components thereof so described are suitable for use in contact with human keratinous tissue without undue toxicity, incompatibility, instability, allergic response, and the like.

"Effective amount" means an amount of a compound or composition sufficient to significantly induce a positive or desired benefit, (e.g., a positive skin or feel benefit, reverse the expression of a gene, group of genes and/or gene expression signature), including independently or in combinations the benefits disclosed herein, but low enough to avoid serious side effects, i.e., to provide a reasonable benefit to risk ratio, within the scope of sound judgment of the skilled artisan.

"Estrogen agent" means any natural or synthetic estrogen hormone (e.g., estrone, estradiol and estriol), metabolites thereof, esters thereof, analogues thereof, phytoestrogens (e.g., isoflavones, coumestans, prenylflavonoids), estrogen precursors (e.g., dehydroepiandrosterone) and/or any compound which binds to an estrogen receptor or which otherwise exhibits at least mild or weak estrogen-like effects, including selective estrogen receptor modulators ("SERM") such as, for example: afioxifene (4-hydroxytamoxifen) arzoxifene, bazedoxifene, clomifene, femarelle (DT56a), lasofoxifene, ormeloxifene, raloxifene, tamoxifen, toremifene, mifepristone (RU486), VA2914, ulipristal, Proellex, Asoprisnil, and CDB-4124.

"Introitus" refers to the vaginal opening and the portion of the vagina extending up to 35 millimeters (mm) into the vaginal canal from the vaginal opening.

"Labia" refers, generally, to the labia majora and the labia minora.

"Menopause" refers to the biological condition where a woman does not experience a menstrual period for 12 consecutive months and no other biological or physiological cause can be identified. Post-menopausal women typically have a blood level of estradiol of less than 30 pg/ml.

"Mucoadhesion" refers to the phenomenon where a natural or synthetic substance applied to a mucosal epithelium adheres to the mucus layer, typically creating a new interface. Generally, mucoadhesion can be achieved via physical or chemical processes or both, for example, as described in J. Controlled Release, Vol. 2 (1982) pp. 257 and J. Controlled Release, Vol. 18 (1992) pp. 249.

"Non-volatile" means that the material exhibits a vapor pressure of less than 0.2 mm Hg at 25° C. and one atmosphere and/or a material that has a boiling point at one atmosphere of at least 300° C.

"Progesterone agent" means any natural or synthetic progesterone hormone, metabolites thereof, analogues thereof, progesterone precursors and/or any compound which binds to a progesterone receptor or which otherwise exhibits at least mild or weak progesterone-like effects, including selective progesterone receptor modulators ("SPRM") such as, for example, telapristone.

"Substantially free" means a component or material is present in amount less than 0.5% (e.g., 0.1%, 0.05%, 0.025%, 0.01%, or even less than 0.001%) by weight of the vaginal care composition.

"Vaginal care agent" means any substance, as well any component or derivative thereof, that is useful for treating or ameliorating one or more symptoms of vaginal dryness and is suitable for application to the introitus, labia, vulva, vestibule, and external urogenital tract.

"Vaginal care composition" means any composition comprising a vaginal care agent.

"Vaginal tissue" means epithelial tissue associated with one or more of the introitus, vulva, vestibule, labia, and external urogenital tract.

"Volatile" means that the material exhibits a vapor pressure of 0.2 mm of mercury or more at 25° C. and one atmosphere.

"Wax" means a silicone or hydrocarbon compound that is solid or pasty at 25° C.

Vaginal Care Composition

The vaginal care compositions herein include an effective amount of a vaginal care agent, and are intended for topical application to the introitus and/or the labia. The vaginal care composition provides a suitable dry feel, moisturization/emolliency, lubricity, and/or vaginal skin health benefit. The vaginal care agent may be combined with a dermatologically acceptable carrier, along with any optional ingredients (e.g., preservatives, rheology modifiers, emulsifiers, humectants, lubricants, moisturizers, feel modifiers, pH agents, emollients, vitamins), using conventional methods of making such compositions. In some instances, the vaginal care composition may be provided in the form of a spreadable gel, serum, lotion, paste or cream.

In some instances, the vaginal care composition may be in the form of an oil-in-water emulsion to provide a sensorial feel that is light and non-greasy, but still delivers moisturization and lubricity without the undesirable feel properties commonly associated with some conventional vaginal care compositions (e.g., stickiness or heavy residue feeling). Suitable oil-in-water emulsions herein may comprise a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. The dispersed oil phase is typically present at less than 30% by weight of composition (e.g., 1% to 20%, 2% to 15%, 3% to 12%, 4% to 10%, or even 5% to 8%) to help avoid some of the undesirable feel effects of oily compositions. The oil phase of the vaginal care compositions herein includes one or more volatile or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

Vaginal Care Agent

The vaginal care compositions herein include 0.0001% to 15% by weight of one or more vaginal care agents (e.g., 0.001% to 15%, 0.01% to 15%, 0.1% to 10%, 0.5% to 7%, or even 1% to 5%). The vaginal care agent(s) may be selected to inhibit, stop, or even reverse a change in gene expression exhibited by the labia and/or introitus during menopause. Since it has now been discovered that the labia majora and introitus undergo markedly different genetic changes during menopause, it may be desirable to specifically select a vaginal care agent for treating the unique changes associated with each of the introitus and labia. It is believed, without being limited by theory, that the vaginal actives disclosed herein, which were previously unknown for use in vaginal care compositions, may provide relief to users suffering from vaginal dryness.

Some nonlimiting examples of vaginal care agents that may be suitable for treating the introitus include a mixture of biotin, linoleic acid, vitamin E, panthenol, and caffeine (e.g., Rovisone Hair Growth Serum™ from Evonik); a mixture of propanediol, lysine, lecithin, phenoxyethanol, tripeptide-9, and citrulline (e.g., dGlyage® from Lipotec); disodium tetramethylhexadecenyl succinyl cysteine (e.g., SIG-1273™ from Signum Dermalogix); glyceryl thioglycolate; *Castanea sativa* (sweet chestnut); *Myrocarpus frondosus* or *Myrocarpus fastigiatus* (cabrueva); *Pistacia lentiscus* gum oil (e.g., Lachestim™ from Codif); glyceryl monoricinoleate (e.g., Ricinolex™ from Taiyo Corporation); pentapeptide-28 (e.g., Chondricare™ IS from Ashland); seppic 2390; *Cinnamomum cassia* (Chinese cinnamon); bamboo; piroctone olamine; and derivatives and combinations of these.

Some non-limiting examples of vaginal care agents that may be suitable for treating the labia majora and/or labia minora include *Paeonia sulfruticosa* (peony); *Castanea sativa*; hydroxydecyl ubiquinone (also known as idebenone); myristoyl octapeptide-1 (e.g., Sympeptide™ 239 from Symrise); hydrolyzed soybean fiber (e.g., PRO-COLL-ONE+® from Silab); yeast extract (e.g., Eternixine® from Ashland); hexapeptide-9 (e.g., Collaxyl™ IS from Ashland); pentapeptide-28; geranyllinalool; algae extracts (e.g., *Gelidium cartilagineum* (red algae) available as Rhodysterol® S from Seppic); menthyl anthranilate; and derivatives and combinations of these.

Some non-limiting examples of vaginal care agents that may be suitable for treating both the introitus and the labia include *Oenothera biennis* (evening primrose) (e.g., Lunawhite™ brand evening primrose seed extract from Ichimaru Pharcos Co.); hyaluronic acid (e.g., Primalhyal™ 300 from Givaudan); tetrapeptide-21 (e.g., TEGO™ Pep 4-17 from Evonik); a mixture of biotin, linoleic acid, vitamin E, panthenol, and caffeine; proanthocyanidin A; arginine aminobenzoate; a mixture of glycolic acid, ascorbyl tetraisopalmitate, and kojic acid (e.g. Unitone® from Isispharma); *Brassica rapa* (Chinese cabbage); farnesene (e.g., one or more isomers of 3,7,11-trimethyl-1,3,6,10-dodecatetraene); dehydrocholesterol; javanol (CAS #198404-98-7); *Castanea sativa; Ballota pseudodictamus* (Greek horehound); dipropyl-7-methylxanthine; *Stachys byzantina* (lamb's ear); 2-decanone; acetyl tetrapeptide-11 (e.g., Syniorage™ from BASF); and derivatives and combinations of these.

The botanical (i.e., plant derived) ingredients herein may be provided as extracts obtained from any suitable part of the plant (e.g., leaf, root, stem, flower, seeds) using methods known to those skilled in the art for making botanical extracts. Additionally or alternatively, fresh and/or dried plant material or serum fractions thereof may be used. Some nonlimiting examples of methods for producing plant extracts and plant serum fractions are disclosed, respectively, in U.S. Pat. Nos. 9,358,263 and 7,442,391.

Optional Ingredients

It may be desirable to include a silicone oil in the vaginal care compositions herein to provide a light, lubricious feel and/or a moisturization benefit to vaginal skin. Silicone oils are typically liquids comprising one or more polymerized siloxanes or silicone polymers (e.g., polysiloxanes, polydimethylsiloxanes (PDMS), or combinations thereof). The silicone oil may be volatile (e.g., cyclomethicone D5) or non-volatile (e.g. dimethicone 50 cSt). The vaginal care composition may comprise 0.1% to 10% (e.g., 0.5% to 8%, 1% to 5% or even 2% to 4%) by weight of the vaginal care composition of silicone oil(s).

In some examples, the vaginal care composition may include a botanical oil derived from one or more plant source materials such as the leaf, root, bark, stem, flower or seed of a plant. The botanical oil may provide an emolliency benefit to vaginal skin. The botanical oil may comprise polyunsaturated fatty acids, preferably omega-3 (e.g., α-linolenic acid) and/or omega-6 fatty acids. Some particularly suitable examples of botanical oil include coconut oil, camelina seed oil, sunflower seed oil, safflower oil and combinations thereof, all of which include omega-3 and/or omega-6 fatty acids. The vaginal care composition may comprise from about 0.1% to about 2%, or from about 0.2% to about 1%, or from about 0.2% to 0.5% by weight of the vaginal care composition of botanical oil(s).

The vaginal care compositions herein may include one or more vitamins and/or pro-vitamins (i.e., a substance that is converted into a vitamin within an organism) for providing a vaginal skin health benefit. Some non-limiting examples of vitamins and pro-vitamins that may be suitable for use herein are disclosed in U.S. Pat. No. 9,676,696. Some particularly suitable examples of vitamins and pro-vitamins that may be suitable for use herein include vitamin B1, panthenol, vitamin B3, vitamin B5, vitamin E, and derivatives thereof (e.g., tocopheryl acetate). Vitamin(s) and/or pro-vitamin(s) may be included in the vaginal care composition at an amount of 0.1% to 7% (e.g., 0.5% to 5%, or even 2% to 4%) by weight of the vaginal care composition.

The vaginal care composition may comprise one or more humectants to provide a moisturizing benefit. An exemplary class of humectants is polyhydric alcohols. Suitable polyhydric alcohols include polyalkylene glycols and alkylene polyols and their derivatives, including propylene glycol, dipropylene glycol, polypropylene glycol, polyethylene glycol; sorbitol; hydroxypropyl sorbitol; erythritol; threitol; pentaerythritol; xylitol; glucitol; mannitol; hexylene glycol; butylene glycol (e.g., 1,3-butylene glycol); pentylene glycol; hexane triol (e.g., 1,2,6-hexanetriol); glycerin; ethoxylated glycerin; and propoxylated glycerin. The humectant may be present at 1% to 20% (e.g., 5% to 15%, or 8% to about 12%) by weight of the vaginal care composition.

The vaginal care composition may include particulate materials for providing a desirable feel property to the composition. The particles, when included, may be spherical or non-spherical and have a mean particle size of less than 125 μm (e.g., less than 100 μm, 75 μm, 50 μm, 40 μm, 30 μm, 20 μm, or even less than 15 μm). In some instances, the particle size may be between 2 μm and 40 μm (e.g., 10 to 25 μm). If the particles are too big, they may feel abrasive when the composition is applied to sensitive vaginal skin. Particle size can be determined by any suitable method known in the art, such as by using Coulter counter equipment, laser diffraction equipment (e.g., LA-960 from Horiba Scientific or the like), dynamic or static image analysis equipment (e.g., Camsizer® from Horiba Scientific or the like), or optical microscopy (e.g., ASTM designation E20-85 titled "Standard Practice for Particle Size Analysis of Particulate Substances in the Range of 0.2 to 75 Micrometers by Optical Microscopy" ASTM Volume 14.02, 1993). The particles, when included, may be present at 0.01% to 25% (e.g., 0.1% to 20%, 0.5% to 15%, 1% to 10%, or even 2% to 8%) by weight.

Some non-limiting examples of particles that may be suitable include polymeric particles chosen from the methylsilsesquioxane resin microspheres (e.g., the TOSPEARL® series of spherical silicone resin beads from Momentive Performance Materials, Inc.); microspheres of polymethylmethacrylates (Micropearl™ M 100 from Seppic); spherical silicone elastomer particles of crosslinked polydimethylsiloxanes (e.g., KSP-100, KSP-101, KSP-102, KSP-103, KSP-104, and KSP-105 all from Shin Etsu; and DC9506 and DC 9701 from Dow Corning); Non-spherical crosslinked siloxane elastomers (e.g., KSG 15 and KSG 16 from Shin Etsu and DC 9040, DC 9041, and DC 9045 from Dow Corning); spherical particles of polyamide (e.g., nylon-12 and Orgasol™ 2002D Nat C05 from Atochem); polystyrene microspheres (e.g., (Dynospheres™ from ThermoFisher Scientific); ethylene acrylate copolymer (e.g., FloBead™ EA209 from Kobo); aluminum starch octenylsuccinate (e.g., the Dry Flo™ of coated and uncoated spherical starch particles from Akzo Nobel); microspheres of polyethylene (e.g., Microthene™ FN510-00 from Equistar), and combinations of these.

Another example of a material that may provide suitable feel properties is a silicone elastomer. A silicone elastomer can help reduce the tackiness of the composition (e.g., caused by non-volatile oils) and provide a more lubricious feel upon application. Some non-limiting examples of silicone elastomers are crosslinked organopolysiloxane (or siloxane) elastomers, as described in U.S. Patent Publication No. 2003/0049212. The elastomers may be emulsifying or non-emulsifying silicone elastomers. "Emulsifying," as used herein, means crosslinked organopolysiloxane elastomers having at least one polyoxyalkylene 30 (e.g., polyoxyethylene or polyoxypropylene) or polyglycerin moiety, whereas "non-emulsifying" means crosslinked organopolysiloxane elastomers essentially free of polyoxyalkylene or polyglycerin moeities. Some non-limiting examples of silicone elastomers that may be suitable for use herein are disclosed in U.S. Publication Nos. 2013/0243835, 2003/0049212, and 2002/0022040; and U.S. Pat. Nos. 5,412,004; 5,837,793; and 5,811,487.

Still other examples of materials that may provide desirable feel properties include low-melting-point waxes (e.g., hydrocarbon waxes and/or silicone waxes). A low-melting-point wax may be selected to impart a dry feel when touched initially and a lubricious feel in use (i.e., upon melting). The low-melting-point wax, upon melting, may also facilitate the ease of spreading, rubbing or otherwise applying the vaginal care composition to vaginal tissue. When a low-melting-point hydrocarbon wax is used, it can create a lamellar gel network that helps thicken the vaginal care composition without creating a mucoadhesive formulation. When a low-melting-point silicone wax is used, it may provide a particularly desirable feel benefit during application by forming a layer of silicone that provides a smooth, slick feel. This can be especially desirable when topically applying a vaginal care composition to sensitive and/or compromised vaginal tissue. In addition, the low-melting-point silicone wax will melt upon application to provide a liquid lubricant that helps with comfort during use/wear. Some non-limiting examples of silicone waxes that may be suitable for use herein are described in U.S. Publication No. 2004/0197286. The melting point of the low-melting-point waxes herein is selected to be less than the average human body temperature, which is typically about 37° C. For example, the low-melting-point wax may have a melting point of between 25° C. and 37° C. (e.g., 28° C. to 35° C.), which can be determined using the drop melting point described in ASTM D127.

The vaginal care compositions herein may include one or more thickeners to provide suitable rheological properties to the composition (e.g., viscosity). Some non-limiting examples of thickeners that may be suitable for use herein include non-acidic gums, starches, modified starches, clays, and cross-linked water swellable polymers; fatty alcohols (e.g., cetearyl glucoside, cetearyl alcohol, behenyl alcohol, cetyl alcohol, stearyl alcohol); and polyacrylamides (e.g., Sepigel™ 305 from Seppic). The thickeners are provided in amounts to facilitate achieving the desired viscosity in combination with the other ingredients in the vaginal care composition. The vaginal care compositions herein may have a viscosity suitable for dispensing onto an applicator without dripping or runniness, especially when the applicator is being manipulated by a user prior to applying the vaginal care composition to the introitus and/or external vaginal tissues. The vaginal care composition may also have a viscosity conducive to spreading onto the vaginal tissues of interest using hand(s), finger(s) and/or an applicator described herein without undue effort. For example, the vaginal care composition may have a viscosity of 2,000 cps to 200,000 cps; in some examples, 5,000 cps to 150,000 cps; and in some examples, 20,000 cps to 90,000 cps, or any range formed by any of the preceding values. The thickeners may be present in the vaginal care composition at 0.1% to 10% (e.g., 0.5% to 8%, 1% to 5%, or even 2% to 4%) by weight of the vaginal care composition. Other non-limiting examples of thickeners are disclosed in U.S. Publication No. 2008/0051497 and U.S. Pat. No. 9,795,552.

In some instances, it may be desirable to exclude from the vaginal care compositions herein thickeners and/or other materials that have hydroxyl or carboxyl functional moieties, which may impart undesirable feel properties (e.g., stickiness, heavy residue feel, non-lubricious feel). Conventional methods of treating vaginal dryness may involve depositing 5 g to 15 g of a mucoadhesive vaginal care composition deep within the vaginal canal using a plunger-style applicator. The formulations used in such treatment methods are intentionally designed to adhere to the vaginal wall to provide a treatment benefit for up to three days. However, when such compositions are applied to the labia and/or introitus, they can feel sticky, heavy, and/or non-lubricious. Accordingly, it may be desirable to formulate the vaginal care compositions herein to be free or substantially free of such materials. Some non-limiting examples of mucoadhesive materials that may be undesirable for use herein include polyacrylates (e.g., Makimousse-12 and -25 brand sodium polyacrylate starch from Kobo), carbomers (e.g., Carbopol® from Lubrizol), polycarbophils (e.g., Noveon® from Lubrizol), poly(methylvinyl ether/maleic anhydride) copolymers, acidic synthetically modified natural polymers (e.g., carboxymethylcellulose), basic amine-bearing polymers (e.g., chitosan); acidic polymers obtainable from natural sources (e.g., alginic acid, pectin, tragacanth gum, and karaya gum); and neutral synthetic polymers (e.g., polyvinyl alcohol and polyvinylpyrrolidone).

While some materials such as hyaluronic acid, sodium hyaluronate, and/or other emollients may provide a desirable moisturization and/or vaginal tissue health benefit, they can also exhibit undesirable mucoadhesive characteristics when included in an aqueous vaginal care composition (e.g., stickiness). Thus, the drawbacks of including a mucoadhesive emollient may outweigh the lubricity and skin health benefit provided by such materials. However, it has now been surprisingly found that a selection of a low level of hyaluronic acid and a polyacrylamide thickener can provide an O/W emulsion-type vaginal composition that is stable and provides the lubrication and skin health benefits without the undesirable sticky feel. For example, the vaginal care compositions herein may include 2% or less by weight of hyaluronic acid (e.g., 0.01% to 2%, 0.1% to 2%, or even 0.5% to 1%). In some instances, it may be desirable to provide a ratio of hyaluronic acid to polyacrylamide of 1:10 to 1:1.

The vaginal care compositions herein are generally free or substantially free of ingredients that may be irritating to vaginal tissues (e.g., certain retinoids, ethanol, sunscreen agents, perfumes, and particulates having an average particle size of more than 125 microns). The vaginal care compositions herein are also free or substantially free of estrogen and/or progesterone agents, due to the undesirable side effects that have been reported for these ingredients.

Methods of Use

The vaginal care compositions herein can be used to treat vaginal dryness by applying the vaginal care composition to the vaginal tissue (e.g., labia and introitus) of a user who is experiencing vaginal dryness (e.g., a peri-menopausal, menopausal, or post-menopausal user). The amount of the vaginal care composition applied to the vaginal tissue may vary, depending on, for example, the amount and/or type of vaginal care agent present in the composition and/or the type or degree of vaginal dryness experienced by the user. In some instances, a user may apply between 0.1 g and 2 g (e.g., 0.2 g to 1.2 g, or about 1 g) to the target vaginal tissue over the course of a treatment period. The vaginal care composition can be applied at least once per day, twice per day, or on a more frequent daily basis, during a treatment period. The treatment period is ideally of sufficient time for the vaginal care agent to provide the desired benefit. For example, the treatment period may last for at least 1 week (e.g., about 2 weeks, 4 weeks, 8 weeks, or even 12 weeks). In some instances, the treatment period will extend over multiple months (i.e., 3-12 months) or multiple years. In some instances, the vaginal care composition may be applied most days of the week (e.g., at least 4, 5 or 6 days a week), at least once a day or even twice a day during a treatment period of at least 2 weeks, 4 weeks, 8 weeks, or 12 weeks.

The vaginal care compositions herein may be applied by any suitable means known for applying such products, including digitally (i.e., with the hands and/or fingers) and/or with a disposable or reusable implement. The user may dispense the vaginal care composition onto a finger, hand, and/or implement and then apply the vaginal care composition to the target vaginal tissue. Additionally or alternatively, the user may dispense the vaginal care composition directly onto the target vaginal tissue and use a finger, hand, and/or implement to spread the vaginal care composition. Some non-limiting example of implements for applying a vaginal care composition include gloves, swabs, wipes, sponges, plunger-style applicators, applicators with a cone-shaped insertion portion, and vaginal rings. A particularly suitable example of an applicators with a cone-shaped insertion portion is the egg-shaped applicator described in co-pending U.S. Provisional Ser. No. 62/622,298. Exemplary methods of using an implement to apply a vaginal care composition are also disclosed in U.S. Provisional Ser. No. 62/622,298.

Example Formulations

Table 1 provides examples of the vaginal care compositions described herein. The composition in Table 1 are oil-in-water emulsions. One and a half kilogram batches of Examples 1-18 are made gravimetrically according to the following procedure:

Aqueous phase (A) is prepared by combining all ingredients in a beaker and heating to 75° C. while stirring with a suitable mixer. Oil Phase (B) is prepared in a separate glass beaker by combining all ingredients and heating to 75° C. while stirring with a suitable stir plate and magnetic stir bar. Acidic aqueous phase (C) is prepared in separate glass beaker by combining all ingredients and heating to 40° C. while stirring with a suitable stir plate and magnetic stir bar.

Once Oil Phase (B) reaches 75° C., it is poured into the Water Phase (A) and milled with a Tekmar mixer for 5 minutes at 10,000 rpm, creating an oil-in-water emulsion. After milling, the heat is turned off and the mixture allowed to cool while stirring with an overhead mixer. When the mixture reaches 60° C., Sepigel™ 305 is added. When the mixture reaches 50° C. the Acidic Aqueous Phase (C) is added. When the mixture reached 45° C., the remaining Finishing Ingredients (D) are added and the mixture is milled with a Tekmar mixer for 2 minutes at 8000 rpm. The resulting oil-in-water emulsion is cooled to room temperature and transferred to a storage container.

TABLE 1

| Ingredient | Ex 1 wt. % | Ex 2 wt. % | Ex 3 wt. % | Ex 4 wt. % | Ex 5 wt. % | Ex 6 wt. % |
|---|---|---|---|---|---|---|
| Aqueous Phase (A) | | | | | | |
| Distilled Water | 67.90 | 62.22 | 62.29 | 63.50 | 50.88 | 59.75 |
| Glycerin | 7.00 | 12.00 | 5.00 | 6.00 | 10.00 | 10.00 |
| Sodium Hyaluronate[1] | 0.10 | 1.00 | 2.00 | 0.75 | 0.50 | 1.00 |
| Disodium EDTA[2] | 0.05 | 0.20 | 0.10 | 0.10 | 0.10 | 0.10 |
| Sodium Benzoate | 0.00 | 0.18 | 0.18 | 0.20 | 0.00 | 0.10 |
| Sodium salicylate | 0.20 | 0.00 | 0.20 | 0.00 | 0.25 | 0.05 |
| *Cinnamomum cassia* (Chinese cinnamon) | 0.50 | 0.00 | 0.10 | 0.00 | 0.00 | 0.00 |
| *Brassica rapa* (Chinese cabbage) Extract | 0.00 | 0.60 | 0.00 | 0.00 | 0.00 | 1.00 |
| Hexapeptide-9[3] | 0.00 | 0.00 | 0.00 | 0.20 | 0.00 | 0.00 |
| Oil Phase (B) | | | | | | |
| *Cocos nucifera* (Coconut) Oil | 0.20 | 0.20 | 0.20 | 0.50 | 0.50 | 0.50 |
| *Helianthus annuus* (Sunflower) Seed Oil | 0.10 | 0.10 | 0.10 | 0.00 | 0.10 | 0.50 |
| *Carthamus tinctorious* (Safflower) Seed Oil | 0.10 | 0.10 | 0.10 | 1.50 | 0.00 | 1.00 |
| Stearyl Dimethicone[4] | 0.00 | 0.05 | 2.00 | 5.00 | 3.00 | 0.00 |
| Tocopheryl Acetate (Vitamin E) | 0.20 | 0.50 | 0.50 | 0.70 | 1.00 | 0.20 |
| Cetearyl Glucoside, Cetearyl Alcohol[5] | 0.25 | 0.20 | 0.20 | 0.40 | 0.20 | 0.25 |
| Cetyl Alcohol | 0.50 | 0.70 | 0.60 | 0.70 | 0.60 | 0.50 |
| Stearyl Alcohol | 1.20 | 1.00 | 0.90 | 1.10 | 0.90 | 1.20 |
| Behenyl Alcohol | 0.80 | 0.80 | 0.90 | 0.50 | 1.20 | 0.50 |
| Polymethylsilsesquioxane[6] | 0.25 | 0.25 | 0.25 | 0.50 | 0.30 | 0.75 |
| Peg-100 Stearate[7] | 0.10 | 0.10 | 0.10 | 0.05 | 0.15 | 0.20 |
| *Castanea sativa* (Sweet Chestnut) | 0.00 | 0.00 | 0.00 | 0.00 | 4.00 | 0.00 |
| Proanthocyanidin A | 0.00 | 0.00 | 0.00 | 0.50 | 0.00 | 0.00 |
| Geranyllinalool | 0.10 | 0.00 | 0.00 | 0.00 | 0.00 | 0.00 |
| Acidic Aqueous Phase (C) | | | | | | |
| Distilled Water | 10.00 | 11.00 | 14.00 | 9.00 | 15.00 | 10.00 |
| Citric Acid | 0.50 | 0.50 | 0.50 | 0.50 | 0.50 | 0.50 |
| Sodium Citrate | 0.60 | 0.60 | 0.60 | 0.60 | 0.60 | 0.60 |
| D-Panthenol | 1.00 | 0.00 | 1.00 | 0.50 | 2.00 | 1.00 |
| Niacinamide | 0.00 | 1.00 | 3.00 | 2.50 | 5.00 | 4.00 |
| Yeast extract[8] | 0.00 | 1.50 | 0.00 | 0.00 | 0.00 | 0.00 |
| Arginine Aminobenzoate | 0.00 | 0.00 | 0.00 | 0.00 | 0.00 | 0.50 |
| Finishing Phase (D) | | | | | | |
| Polyacrylamide(and)C13-14 Isoparaffin(and)Laureth-7[9] | 2.50 | 3.00 | 3.00 | 3.50 | 1.00 | 4.50 |
| Phenoxyethanol | 0.15 | 0.00 | 0.00 | 0.00 | 0.00 | 0.10 |
| Dimethicone and Dimethiconol[10] | 5.00 | 2.00 | 2.00 | 1.00 | 2.00 | 1.00 |
| Sorbitan Caprylate[11] | 0.20 | 0.20 | 0.18 | 0.20 | 0.22 | 0.20 |
| Disodium Tetramethylhexadecenyl Succinyl Cysteine[12] | 0.50 | 0.00 | 0.00 | 0.00 | 0.00 | 0.00 |

| Ingredient | Ex 7 wt. % | Ex 8 wt. % | Ex 9 wt. % | Ex 10 wt. % | Ex 11 wt. % | Ex 12 wt. % |
|---|---|---|---|---|---|---|
| Aqueous Phase (A) | | | | | | |
| Distilled Water | 69.10 | 55.87 | 52.62 | 57.85 | 63.65 | 66.42 |
| Glycerin | 2.00 | 15.00 | 9.00 | 9.00 | 7.50 | 5.00 |
| Sodium Hyaluronate[1] | 1.50 | 0.50 | 0.50 | 0.75 | 0.20 | 0.25 |
| Disodium EDTA[2] | 0.10 | 0.10 | 0.10 | 0.10 | 0.20 | 0.10 |
| Sodium Benzoate | 0.00 | 0.18 | 0.18 | 0.00 | 0.18 | 0.18 |
| Sodium salicylate | 0.20 | 0.00 | 0.20 | 0.20 | 0.00 | 0.20 |
| *Gelidium cartilagineum* (Red Algae)[13] | 0.00 | 0.00 | 2.50 | 0.00 | 0.00 | 0.00 |
| *Ballota pseudodictamus* (Greek Horehound) | 1.00 | 0.40 | 0.00 | 0.00 | 0.00 | 0.00 |

TABLE 1-continued

| Oil Phase (B) | | | | | | |
|---|---|---|---|---|---|---|
| *Cocos nucifera* (Coconut) Oil | 1.00 | 1.00 | 0.50 | 0.25 | 0.80 | 0.80 |
| *Helianthus annuus* (Sunflower) Seed Oil | 0.10 | 0.10 | 0.10 | 0.75 | 0.20 | 0.00 |
| *Carthamus tinctorious* (Safflower) Seed Oil | 0.10 | 0.10 | 0.10 | 0.25 | 1.00 | 0.25 |
| Stearyl Dimethicone[4] | 1.00 | 1.00 | 1.00 | 1.00 | 1.50 | 0.50 |
| Tocopheryl Acetate (Vitamin E) | 0.50 | 0.50 | 0.50 | 0.00 | 0.10 | 0.50 |
| Cetearyl Glucoside, Cetearyl Alcohol[5] | 0.20 | 0.20 | 0.20 | 0.20 | 0.20 | 0.20 |
| Cetyl Alcohol | 0.60 | 0.60 | 0.60 | 0.60 | 0.60 | 0.60 |
| Stearyl Alcohol | 0.95 | 0.95 | 0.95 | 0.95 | 0.95 | 0.95 |
| Behenyl Alcohol | 0.80 | 0.80 | 0.80 | 1.00 | 1.10 | 0.70 |
| Polymethylsilsesquioxane[6] | 0.25 | 0.30 | 0.25 | 0.60 | 0.50 | 0.80 |
| Peg-100 Stearate[7] | 0.15 | 0.10 | 0.10 | 0.20 | 0.15 | 0.10 |
| Menthyl Anthranilate | 0.00 | 0.00 | 1.00 | 0.00 | 0.00 | 0.00 |
| 2-decanone | 0.00 | 0.00 | 0.00 | 5.00 | 0.00 | 0.00 |
| *Oenothera biennis* (Evening Primrose) Extract[14] | 0.00 | 0.00 | 0.00 | 0.00 | 0.00 | 2.50 |
| Glyceryl Monoricinoleate[15] | 1.00 | 0.00 | 0.00 | 0.00 | 0.00 | 0.00 |
| Acidic Aqueous Phase (C) | | | | | | |
| Distilled Water | 10.00 | 12.00 | 15.00 | 10.00 | 14.00 | 10.00 |
| Citric Acid | 0.50 | 0.50 | 0.50 | 0.50 | 0.50 | 0.50 |
| Sodium Citrate | 0.60 | 0.60 | 0.60 | 0.60 | 0.60 | 0.60 |
| D-Panthenol | 1.00 | 1.00 | 1.00 | 2.50 | 0.50 | 0.00 |
| Niacinamide | 2.00 | 3.00 | 3.00 | 2.50 | 1.00 | 4.00 |
| Glyceryl Thioglycolate | 0.00 | 0.00 | 3.50 | 0.00 | 0.00 | 0.00 |
| Finishing Phase (D) | | | | | | |
| Polyacrylamide(and)C13-14 Isoparaffin(and)Laureth-7[9] | 3.00 | 3.00 | 3.00 | 2.00 | 3.00 | 3.50 |
| Phenoxyethanol | 0.15 | 0.00 | 0.00 | 0.05 | 0.15 | 0.10 |
| Dimethicone and Dimethiconol[10] | 2.00 | 2.00 | 2.00 | 3.00 | 1.00 | 1.00 |
| Sorbitan Caprylate[11] | 0.20 | 0.20 | 0.20 | 0.15 | 0.22 | 0.25 |
| Myristoyl Octapeptide-1[16] | 0.00 | 0.00 | 0.00 | 0.00 | 0.20 | 0.00 |

| Ingredient | Ex 13 wt. % | Ex 14 wt. % | Ex 15 wt. % | Ex 16 wt. % | Ex 17 wt. % | Ex 18 wt. % |
|---|---|---|---|---|---|---|
| Aqueous Phase (A) | | | | | | |
| Distilled Water | 69.70 | 65.40 | 67.22 | 60.35 | 59.81 | 60.52 |
| Glycerin | 3.00 | 4.00 | 5.00 | 5.00 | 10.00 | 9.00 |
| Sodium Hyaluronate[1] | 0.50 | 0.50 | 0.10 | 0.10 | 0.50 | 2.00 |
| Disodium EDTA[2] | 0.10 | 0.30 | 0.10 | 0.10 | 0.10 | 0.15 |
| Sodium Benzoate | 0.00 | 0.20 | 0.18 | 0.15 | 0.19 | 0.15 |
| Sodium salicylate | 0.20 | 0.05 | 0.20 | 0.00 | 0.00 | 0.05 |
| *Paeonia suffruticosa* (Peony) | 0.00 | 3.00 | 0.00 | 0.00 | 0.00 | 0.00 |
| Tetrapeptide-21[17] | 0.10 | 0.00 | 0.00 | 0.00 | 0.00 | 0.00 |
| Oil Phase (B) | | | | | | |
| *Cocos nucifera* (Coconut) Oil | 0.20 | 0.20 | 0.20 | 0.20 | 0.20 | 0.20 |
| *Helianthus annuus* (Sunflower) Seed Oil | 0.10 | 0.10 | 0.10 | 1.00 | 0.50 | 0.75 |
| *Carthamus tinctorious* (Safflower) Seed Oil | 0.10 | 0.10 | 0.10 | 0.10 | 2.00 | 0.50 |
| Stearyl Dimethicone[4] | 1.00 | 0.00 | 1.00 | 2.00 | 1.00 | 1.00 |
| Tocopheryl Acetate (Vitamin E) | 0.50 | 0.50 | 0.50 | 1.00 | 0.25 | 0.50 |
| Cetearyl Glucoside, Cetearyl Alcohol[5] | 0.20 | 0.20 | 0.20 | 0.30 | 0.40 | 0.10 |
| Cetyl Alcohol | 0.70 | 0.60 | 0.60 | 0.80 | 0.40 | 0.20 |
| Stearyl Alcohol | 1.00 | 0.90 | 0.90 | 1.10 | 0.80 | 1.00 |
| Behenyl Alcohol | 0.80 | 0.80 | 0.80 | 0.80 | 0.60 | 1.00 |
| Polymethylsilsesquioxane[6] | 0.25 | 0.25 | 0.40 | 0.20 | 0.90 | 1.20 |
| Peg-100 Stearate[7] | 0.10 | 0.10 | 0.10 | 0.30 | 0.25 | 0.20 |
| Hydroxydecyl Ubiquinone | 0.00 | 0.00 | 0.00 | 0.00 | 0.00 | 0.30 |
| Hydrolyzed Soybean Fiber[18] | 0.00 | 0.00 | 2.00 | 0.00 | 0.00 | 0.00 |
| Javanol | 0.00 | 0.00 | 0.00 | 0.20 | 0.00 | 0.00 |
| Acidic Aqueous Phase (C) | | | | | | |
| Distilled Water | 11.00 | 12.00 | 10.00 | 15.00 | 10.00 | 10.00 |
| Citric Acid | 0.50 | 0.50 | 0.50 | 0.50 | 0.50 | 0.50 |
| Sodium Citrate | 0.60 | 0.60 | 0.60 | 0.60 | 0.60 | 0.60 |
| D-Panthenol | 1.00 | 1.00 | 1.00 | 1.50 | 0.80 | 1.20 |
| Niacinamide | 3.00 | 3.00 | 3.00 | 3.00 | 4.00 | 2.00 |
| *Stachys Byzantina* (Lamb's Ear) | 0.00 | 1.00 | 0.00 | 0.00 | 0.00 | 0.00 |
| Dipropyl-7-Methylxanthine | 0.00 | 0.00 | 0.00 | 2.00 | 0.00 | 0.00 |

TABLE 1-continued

| Finishing Phase (D) | | | | | | |
|---|---|---|---|---|---|---|
| Polyacrylamide(and)C13-14 Isoparaffin(and)Laureth-7[9] | 3.00 | 2.50 | 3.00 | 2.50 | 1.50 | 3.50 |
| Phenoxyethanol | 0.15 | 0.00 | 0.00 | 0.00 | 0.00 | 0.18 |
| Dimethicone and Dimethiconol[10] | 2.00 | 2.00 | 2.00 | 1.00 | 2.50 | 3.00 |
| Sorbitan Caprylate[11] | 0.20 | 0.20 | 0.20 | 0.20 | 0.20 | 0.20 |
| A mixture of Propanediol, Lysine, Lecithin, Phenoxyethanol, Tripeptide-9, and Citrulline[19] | 0.00 | 0.00 | 0.00 | 0.00 | 2.00 | 0.00 |

[1] Available as Bio-Sodium Hyaluronate Powder from SK Bioland (South Korea).
[2] Available as Dissolvine ® Na2-S from Akzo Nobel Functional Chemicals (Chicago, IL).
[3] Available as Collaxyl ™ IS from Ashland, Inc.
[4] Available as Silwax ® D118 from Siltech (Toronto, Canada).
[5] Available as Emulgade ® PL68/50 from BASF (Cincinnati, OH).
[6] Available as CF600 from Momentive Performance Materials (Waterford, NY).
[7] Available as Lipopeg ® 100-S from Lipo Chemicals (Warren Township, NJ).
[8] Available as Etemixine ® from Ashland, Inc.
[9] Available as Sepigel ™ 305 from Seppic (Fairfield, NJ).
[10] Available as DC 1503 from Dow Corning ® Corp. (Carrollton, KY).
[11] Available as Velsan ® SC from Clariant (Muttenz, Switzerland).
[12] Available as SIG-1273 ™ from Signum Dermalogix
[13] Available as Rhodysterol ® S from Seppic (Fairfield, NJ)
[14] Available as Lunawhite ™ brand evening primrose seed extract from Ichimaru Pharcos Co.
[15] Available as Ricinolex ™ from Taiyo Corporation
[16] Available as Sympeptide ™ 239 from Symrise
[17] Available as TEGO ™ Pep 4-17 from Evonik
[18] Available as PRO-COLL-ONE+ ® from Silab
[19] Available as dGlyage ® from Lipotec

Vaginal Dryness Gene Expression Study

A study was conducted to determine the effect of menopausal and hormone therapy status on the introitus and labia majora at the level gene expression. Three cohorts of ten healthy women each were selected for this study and included (1) pre-menopausal women showing little to no sign of clinical urogenital atrophy and having a vaginal pH <5.0 (Pre-M); (2) post-menopausal women showing signs of clinical urogenital atrophy and having a vaginal pH ≥5.0 (Post-M); and (3) post-menopausal women on systemic hormone therapy showing little to no sign of clinical urogenital atrophy and having a vaginal pH <5.0 (Post-M+HT). Vaginal pH was measured using pH paper. Each subject completed a questionnaire that probed presence and magnitude of symptoms associated with urogenital atrophy. These included vaginal dryness, genital skin (external) dryness, vaginal itch, genital skin (external) itch, and difficulty having intercourse. Symptoms were rated on a scale of none (0), slight (1), moderate (2), considerable (3), and unbearable (4).

Biopsies were obtained from the introitus (fourchette) and labia majora and processed for transcriptomic analyses. Full thickness tissue samples for transcriptomic analysis were initially placed in RNALater (ThermoFisher Scientific, Waltham, Mass.) and then frozen and processed using standard techniques for RNA extraction, preparation of labelled cRNA and analysis using Affymetrix (Santa Clara, Calif.) GeneTitan® U219 array plates according to the manufacturer's protocols. Other data collected included self-assessed symptoms, blood estradiol, testosterone, and serum hormone binding globulin (SHBG), and the pH of the labia majora.

Constructing a Gene Expression Signature for the Introitus and Labia Majora.

Generally, a gene expression signature may be constructed by (a) obtaining a gene expression profile for the vaginal tissue sample of interest (e.g., the introitus and/or labia), for example, via microarray analysis; (b) identifying genes differentially expressed in the sample by comparing the gene expression profile of (a) with gene expression measurements for a control sample (e.g., an equivalent tissue sample from non-menopausal subject); (c) causing a computer to calculate a gene expression consistency value that is representative of the significance of the difference in expression in (b). The gene expression consistency value may be calculated by comparing log-odds ratios computed for the differentially expressed genes, and transforming the log-odds ratios using a sigmoid function. In some examples, a one-tailed t-test against zero may be performed and log-odds ratios may be computed from the one-tailed t-test. The resulting gene expression consistency value is used to generate an ordered list of identifiers representing genes that are differentially expressed. The ordered list of identifiers is optionally associated with a numerical ranking for the identifier corresponding to its rank in the ordered list. The method may further include (d) creating an ordered list comprising identifiers representing consistently differentially expressed genes (i.e., genes differentially expressed in the tested biological conditions compared to the control sample), wherein the identifiers are ordered according to the gene expression consistency value computed in (c); and (e) storing the ordered list as a gene expression signature on at least one computer readable medium. Any one or more of steps (b), (c), (d), or (e) may be performed with a programmable computer. Some non-limiting example of constructing gene expression signatures are described in U.S. Pat. No. 9,434,993 and U.S. Publication No. 2017/0343534.

Gene expression data from the vaginal dryness study described above was analyzed to construct a gene expression signature for the atrophied introitus and labia majora. In general, comparisons were made between the gene expression profiles of the post-menopausal groups with dryness to the other groups without dryness (either pre-menopausal or post-menopausal+HRT). The gene expression data for the introitus and labia majora were analyzed separately to generate a gene expression signature for each. For each sample site (i.e., introitus and labia majora) probe sets were selected by filtering for p <0.01 in either the Post-M to Pre-M or the Post-M to Post-M+HT comparisons (i.e., dryness to non-dryness). Additional filtering was done to eliminate probe sets with low signal. The top 200 most statistically significant probe sets (100 up-regulated and 100 down-regulated) based on the t-statistic (p-value) were selected for use as the gene expression signatures.

The results of the study indicate that the introitus appears sensitive to menopause/hormone therapy status. Changes that were observed included a thinning of the epithelium in post-menopausal subjects with vaginal atrophy and differential expression of many genes likely to contribute to tissue remodeling in the atrophic introitus. Levels of expression of genes associated with wounding, angiogenesis, cell migration/locomotion, dermal structure, apoptosis, inflammation, epithelial cell differentiation, and fatty acid, carbohydrate, and steroid metabolism were different in atrophied versus non-atrophied introitus tissue samples. Changes were also observed at the labia, but that site appeared less sensitive to menopause/hormone therapy status. The introitus displayed many similarities with the histological and transcriptomic changes in the vagina that are associated with atrophy and HT treatment. The results are believed to indicate that the transcriptomic changes occurring within the introitus during menopause likely contribute to the symptom presentation associated with menopause.

Gene Expression Connectivity Between Vaginal Dryness Gene Expression Signatures and a Database of Vaginal Care Agents.

The gene expression signatures constructed from gene expression analysis data from the introitus and labia majora tissue samples were used to query a connectivity mapping (CMap) database. The Cmap database comprises gene expression profiles from fibroblast (BJ fibroblasts or BJF) and keratinocyte (tert-keratinocytes or tKC) cell lines exposed to a wide variety of different compounds (i.e., "instances"). Some of the compounds in the database are used to treat skin and other diseases or are used in cosmetic products. Some of the compounds in the database have no history of use in drugs or cosmetic products. Methods of constructing and querying a CMap database are described in U.S. Pat. No. 9,434,993 and U.S. Publication No. 2017/0343534. Table 2 shows the top "hits" for each of the introitus gene signature, labia majora gene signature, and the combination of the introitus and labia, based on connectivity score. It may be desirable to include one or more of these actives in a vaginal care composition.

TABLE 2

| Introitus | Cell line | Labia Majora | Cell line | Introitus and Labia Majora | Cell line |
|---|---|---|---|---|---|
| mixture of biotin, linoleic acid, vitamin E, panthenol, and caffeine | tKC | *Paeonia suffruticosa* (peony) | tKC | *Oenothera biennis* | tKC |
| mixture of propanediol, lysine, lecithin, phenoxyethanol, Tripeptide-9, and citrulline | tKC | *Castanea sativa* (sweet chestnut) | tKC | hyaluronic acid | tKC |
| disodium tetramethylhexadecenyl succinyl cysteine | tKC | hydroxydecyl ubiquinone | tKC | hydroxydecyl ubiquinone | tKC |
| glyceryl thioglycolate | tKC | myristoyl octapeptide-1 | BJF | tetrapeptide-21 | tKC |
| *Castanea sativa* (sweet chestnut) | tKC | hydrolyzed soybean fiber | BJF | mixture of biotin, linoleic acid, vitamin E, panthenol, and caffeine | tKC |
| *Myrocarpus frondosus* (cabrueva) | tKC | yeast extract | BJF | proanthocyanidin A | tKC |
| *Myrocarpus Fastigiatus* (cabrueva) | tKC | hexapeptide-9 | BJF | arginine aminobenzoate | tKC |
| *Pistacia lentiscus* gum oil | tKC | pentapeptide-28 | BJF | mixture of glycolic acid, ascorbyl tetraisopalmitate, and kojic acid | tKC |
| glyceryl monoricinoleate | tKC | geranyllinalool | BJF | *Brassica rapa* (Chinese cabbage) | tKC |
| pentapeptide-28 | BJF | Gelidium cartilagineum (red algae) | | piroctone olamine | tKC |
| seppic 2390 | BJF | menthyl anthranilate | | algae | tKC |
| *Cinnamomum cassia* (Chinese cinnamon) | BJF | | BJF | farnesene | BJF |
| bamboo | BJF | | BJF | dehydrocholesterol | BJF |
| | | | | javanol | BJF |
| | | | | *Castanea sativa* (sweet chestnut) | BJF |
| | | | | *Ballota pseudodictamus* (Greek horehound) | BJF |
| | | | | dipropyl-7-methylxanthine | BJF |
| | | | | *Stachys byzantina* (lamb's ear) | BJF |
| | | | | 2-decanone | BJF |
| | | | | acetyl tetrapeptide-11 | BJF |

A method to evaluate whether specific gene expression signatures or group comparisons are yielding meaningful results in connectivity mapping is to determine whether known benchmarks or other agents with known relevant mechanisms link beneficially to the condition signatures. Co-pending Provisional App. Ser. No. 62/666,948, filed by Hodgdon, et al., on May 4, 2018 discusses the predictability of CMap queries for identifying vaginal care actives. Overall, the results support the predictability of the CMap analysis methods described herein.

Examples and Combinations

A. A method of treating vaginal dryness, comprising: administering a vaginal care composition to vaginal tissue of a user experiencing vaginal dryness, wherein the vaginal care composition comprises an effective amount of a vaginal care agent selected from disodium tetramethylhexadecenyl succinyl cysteine, *Castanea sativa, Myrocarpus frondosus, Myrocarpus fastigiatus, Pistacia lentiscus* gum oil, glyceryl monoricinoleate, pentapeptide-28, *Cinnamomum cassia*, bamboo, *Paeonia suffruticosa*, hydroxydecyl ubiquinone, myristoyl octapeptide-1, hydrolyzed soybean fiber, yeast extract, hexapeptide-9, geranyllinalool, *Gelidium cartilagineum*, menthyl anthranilate, *Oenothera biennis*, hyaluronic acid, tetrapeptide-21, proanthocyanidin A, arginine aminobenzoate, a mixture of glycolic acid, ascorbyl tetraisopalmitate, and kojic acid, *Brassica rapa*, farnesene, dehydrocholesterol, javanol, *Ballota pseudodictamus*, dipropyl-7-methylxanthine, *Stachys byzantina*, 2-decanone, a mixture of biotin, linoleic acid, vitamin E, panthenol, and caffeine, a mixture of propanediol, lysine, lecithin, phenoxyethanol, tripeptide-9, and citrulline, acetyl tetrapeptide-11, algae extract, piroctone olamine, and derivatives and combinations of these.

B. The method of paragraph A, wherein the vaginal care agent is present at an amount of about 0.0001% to about 15%.

C. The method of paragraph A or B, wherein the composition is in the form of an oil-in-water emulsion.

D. The method of paragraph C, wherein the oil phase comprises a non-volatile oil.

E. The method of paragraph D, wherein the non-volatile oil is selected from non-volatile silicone oil, coconut oil, camelina seed oil, sunflower seed oil, safflower oil and combinations thereof.

F. The method of any preceding paragraph, wherein the vaginal care composition comprises substantially spherical particles selected from spherical starch particles and spherical silicone elastomer particles.

G. The method of paragraph F, wherein the ratio of non-volatile oil to silicone elastomer particles is 1:10 to 3:2.

H. The method of paragraph F or G, wherein the substantially spherical particles have a mean particle size of about 2 microns to about 40 microns.

I. The method of any preceding paragraph, wherein the composition comprises a humectant.

J. The method of any preceding paragraph, wherein the vaginal care composition comprises about 0.1% to about 20% by weight of a silicone elastomer.

K. The method of any preceding paragraph, wherein the vaginal care composition is substantially free of vaginal irritants selected from retinoids, ethanol, sunscreen agents, perfumes, estrogen, progesterone, particulates having an average particle size of greater than about 125 microns, and combinations of these.

L. The method of any preceding paragraph, wherein the vaginal care composition is administered by the user during a treatment period sufficient to improve the symptom of vaginal dryness.

M. The method of paragraph L, wherein the treatment period is at least 4 weeks.

N. The method of paragraph L or M, wherein the vaginal care composition is applied at least two times per week during the treatment period.

O. The method of any preceding paragraph, wherein the vaginal care composition is substantially free of a mucoadhesive agent selected from polyacrylates, carbomers, polycarbophils poly(methylvinyl ether/maleic anhydride) copolymers, acidic synthetically modified natural polymers, basic amine-bearing polymers, acidic polymers obtainable from natural sources, and neutral synthetic polymers.

P. The method of any preceding paragraph, wherein the vaginal care composition comprises wax particles having a melting of between about 25° C. and about 37° C.

Q. The method of any preceding paragraph, wherein the vaginal care composition comprises hyaluronic acid or a salt thereof in an amount of about 0.01% to about 10% and a polyacrylamide thickener.

R. The method of paragraph Q, wherein the ratio of hyaluronic acid to polyacrylamide thickener is 1:10 to 1:1.

S. A method of treating vaginal dryness, comprising: administering a vaginal care composition to at least one of the vaginal introitus and the labia majora of a user experiencing a symptom of vaginal dryness, wherein the vaginal care composition comprises an effective amount of a vaginal care agent selected from *Oenothera biennis*, hyaluronic acid, tetrapeptide-21, proanthocyanidin A, arginine aminobenzoate, a mixture of glycolic acid, ascorbyl tetraisopalmitate, and kojic acid, *Brassica rapa*, farnesene, dehydrocholesterol, javanol, *Ballota pseudodictamus*, dipropyl-7-methylxanthine, *Stachys byzantina*, 2-decanone, acetyl tetrapeptide-11, algae extract, and derivatives and combinations of these.

T. The method of paragraph S, wherein the female user is menopausal or post-menopausal.

U. The method of paragraph S or T, wherein the vaginal care composition is applied with a topical applicator selected from gloves, swabs, wipes, sponges, plunger-style applicators, applicators with a cone-shape insertion portion, and vaginal rings.

V A method of treating vaginal dryness, comprising:
  a. administering a first vaginal care composition to the introitus of a female user who is experiencing a vaginal dryness condition, wherein the first composition is selected from a mixture of biotin, linoleic acid, vitamin E, panthenol, and caffeine; a mixture of propanediol, lysine, lecithin, phenoxyethanol, tripeptide-9, and citrulline, disodium tetramethylhexadecenyl succinyl cysteine, glyceryl thioglycolate, *Castanea sativa, Myrocarpus frondosus, Myrocarpus fastigiatus, Pistacia lentiscus* gum oil, glyceryl monoricinoleate, pentapeptide-28, *Cinnamomum cassia*, bamboo, piroctone olamine, and derivatives and combinations of these; and
  b. administering a second vaginal care composition to at least one of the labia majora and labia minora of a female user who is experiencing a vaginal dryness condition, wherein the second composition comprises a vaginal care agent selected from *Paeonia suffruticosa, Castanea sativa*, hydroxydecyl ubiquinone, myristoyl octapeptide-1, hydrolyzed soybean fiber, yeast extract, hexapeptide-9, pentapeptide-28, geranyllinalool, rhodysterol, menthyl anthranilate, and derivatives and combinations of these.

W. The method of paragraph V, wherein at least one of the first and second compositions is an oil-in-water emulsion, and the oil phase of the oil-in-water emulsion is less than about 30% by weight of the composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating vaginal dryness, comprising: administering a vaginal care composition to vaginal tissue of a user experiencing vaginal dryness, wherein the vaginal care composition comprises spherical particles having a mean particle size of about 2 microns to about 40 microns and selected from the group consisting of spherical starch particles, spherical silicone elastomer particles, and mixtures thereof, and an effective amount of a vaginal care agent selected from disodium tetramethylhexadecenyl succinyl cysteine, *Castanea sativa, Myrocarpus frondosus, Myrocarpus fastigiatus, Pistacia lentiscus* gum oil, glyceryl monoricinoleate, pentapeptide-28, *Cinnamomum cassia*, bamboo, *Paeonia suffruticosa*, hydroxydecyl ubiquinone, myristoyl octapeptide-1, hydrolyzed soybean fiber, yeast extract, hexapeptide-9, geranyllinalool, *Gelidium cartilagineum*, menthyl anthranilate, *Oenothera biennis*, hyaluronic acid, tetrapeptide-21, proanthocyanidin A, arginine aminobenzoate, a mixture of glycolic acid, ascorbyl tetraisopalmitate, and kojic acid, *Brassica rapa*, farnesene, dehydrocholesterol, javanol, *Ballota pseudodictamus*, dipropyl-7-methylxanthine, *Stachys byzantina*, 2-decanone, a mixture of biotin, linoleic acid, vitamin E, panthenol, and caffeine, a mixture of propanediol, lysine, lecithin, phenoxyethanol, tripeptide-9, acetyl tetrapeptide-11, algae extracts, piroctone olamine, citrulline, and derivatives and combinations of these.

2. The method of claim 1, wherein the vaginal care agent is present at an amount of about 0.0001% to about 15%.

3. The method of claim 1, wherein the composition is in the form of an oil-in-water emulsion.

4. The method of claim 3, wherein the oil phase comprises a non-volatile oil selected from non-volatile silicone oil, camelina seed oil, sunflower seed oil, safflower oil and combinations thereof.

5. The method of claim 4, wherein the spherical particles are spherical silicone elastomer particles and wherein the ratio of non-volatile oil to silicone elastomer particles is about 1:10 to about 3:2.

6. The method of claim 1, wherein the vaginal care composition comprises a humectant.

7. The method of claim 1, wherein the vaginal care composition comprises about 0.1% to about 20% by weight of a silicone elastomer.

8. The method of claim 1, wherein the vaginal care composition is substantially free of vaginal irritants selected from retinoids, ethanol, sunscreen agents, perfumes, estrogen, progesterone, particulates having an average particle size of greater than about 125 microns, and combinations of these.

9. The method of claim 1, wherein the vaginal care composition is administered by the user during a treatment period sufficient to improve the symptom of vaginal dryness.

10. The method of claim 9, wherein the treatment period is at least about 4 weeks.

11. The method of claim 9, wherein the vaginal care composition is applied at least two times per week during the treatment period.

12. The method of claim 1, wherein the vaginal care composition is substantially free of a mucoadhesive agent selected from polyacrylates, carbomers, polycarbophils poly (methylvinyl ether/maleic anhydride) copolymers, acidic synthetically modified natural polymers, basic amine-bearing polymers, acidic polymers obtainable from natural sources, and neutral synthetic polymers.

13. A method of treating vaginal dryness, comprising: administering a vaginal care composition to vaginal tissue of a user experiencing vaginal dryness, wherein the vaginal care composition comprises wax particles having a melting point of between about 25° C. and about 37° C. and an effective amount of a vaginal care agent selected from disodium tetramethylhexadecenyl succinyl cysteine, *Castanea sativa, Myrocarpus frondosus, Myrocarpus fastigiatus, Pistacia lentiscus* gum oil, glyceryl monoricinoleate, pentapeptide-28, *Cinnamomum cassia*, bamboo, *Paeonia suffruticosa*, hydroxydecyl ubiquinone, myristoyl octapeptide-1, hydrolyzed soybean fiber, yeast extract, hexapeptide-9, geranyllinalool, *Gelidium cartilagineum*, menthyl anthranilate, *Oenothera biennis*, hyaluronic acid, tetrapeptide-21, proanthocyanidin A, arginine aminobenzoate, a mixture of glycolic acid, ascorbyl tetraisopalmitate, and kojic acid, *Brassica rapa*, farnesene, dehydrocholesterol, javanol, *Ballota pseudodictamus*, dipropyl-7-methylxanthine, *Stachys byzantina*, 2-decanone, a mixture of biotin, linoleic acid, vitamin E, panthenol, and caffeine, a mixture of propanediol, lysine, lecithin, phenoxyethanol, tripeptide-9, acetyl tetrapeptide-11, algae extracts, piroctone olamine, citrulline, and derivatives and combinations of these.

14. A method of treating vaginal dryness, comprising: administering a vaginal care composition to vaginal tissue of a user experiencing vaginal dryness, wherein the vaginal care composition comprises hyaluronic acid or a salt thereof in an amount of about 0.01% to about 10% and a polyacrylamide thickener, wherein the ratio of hyaluronic acid to polyacrylamide thickener is about 1:10 to about 1:1, and an effective amount of a vaginal care agent selected from disodium tetramethylhexadecenyl succinyl cysteine, *Castanea sativa*, *Myrocarpus frondosus*, *Myrocarpus fastigiatus*, *Pistacia lentiscus* gum oil, glyceryl monoricinoleate, pentapeptide-28, *Cinnamomum cassia*, bamboo, *Paeonia suffruticosa*, hydroxydecyl ubiquinone, myristoyl octapeptide-1, hydrolyzed soybean fiber, yeast extract, hexapeptide-9, geranyllinalool, *Gelidium cartilagineum*, menthyl anthranilate, *Oenothera biennis*, hyaluronic acid, tetrapeptide-21, proanthocyanidin A, arginine aminobenzoate, a mixture of glycolic acid, ascorbyl tetraisopalmitate, and kojic acid, *Brassica rapa*, farnesene, dehydrocholesterol, javanol, *Ballota pseudodictamus*, dipropyl-7-methylxanthine, *Stachys byzantina*, 2-decanone, a mixture of biotin, linoleic acid, vitamin E, panthenol, and caffeine, a mixture of propanediol, lysine, lecithin, phenoxyethanol, tripeptide-9, acetyl tetrapeptide-11, algae extracts, piroctone olamine, citrulline, and derivatives and combinations of these.

15. The method of claim 1, wherein the vaginal care composition is applied with a topical applicator selected from gloves, swabs, wipes, sponges, plunger-style applicators, applicators with a cone-shaped insertion portion, and vaginal rings.

16. The method of claim 13, wherein the vaginal care composition is applied with a topical applicator selected from gloves, swabs, wipes, sponges, plunger-style applicators, applicators with a cone-shaped insertion portion, and vaginal rings.

17. The method of claim 14, wherein the vaginal care composition is applied with a topical applicator selected from gloves, swabs, wipes, sponges, plunger-style applicators, applicators with a cone-shaped insertion portion, and vaginal rings.

\* \* \* \* \*